United States Patent [19]

Dasgupta et al.

[11] Patent Number: 5,045,204
[45] Date of Patent: Sep. 3, 1991

[54] METHOD AND APPARATUS FOR GENERATING A HIGH PURITY CHROMATOGRAPHY ELUENT

[75] Inventors: Purnendu K. Dasgupta; Douglas L. Strong, both of Lubbock, Tex.; John R. Stillian, Pleasanton; Keith A. Friedman, San Jose, both of Calif.

[73] Assignee: Dionex Corporation, Sunnyvale, Calif.

[21] Appl. No.: 479,446

[22] Filed: Feb. 13, 1990

[51] Int. Cl.$^5$ .............................................. B01D 15/08
[52] U.S. Cl. ................................ 210/635; 210/656; 210/748; 210/198.2; 210/243; 204/301; 204/182.4
[58] Field of Search .............. 204/182.4, 182.5, 301; 210/198.2, 635, 656, 748, 243

[56] References Cited

U.S. PATENT DOCUMENTS

| | | | |
|---|---|---|---|
| 3,869,376 | 3/1975 | Tejeda | 204/301 |
| 3,905,886 | 9/1975 | Wang | 204/301 |
| 3,964,985 | 6/1976 | Giuffrida | 204/301 |
| 3,994,799 | 11/1976 | Yao et al. | 204/301 |
| 4,403,039 | 9/1983 | Ban et al. | 210/198.2 |
| 4,459,357 | 7/1984 | Jansen et al. | 210/656 |
| 4,713,156 | 12/1987 | Gal et al. | 204/301 |
| 4,751,189 | 6/1988 | Rocklin | 204/301 |
| 4,804,451 | 2/1989 | Palmer | 204/301 |
| 4,806,219 | 2/1989 | Yamamoto et al. | 204/301 |
| 4,861,555 | 8/1989 | Mowery, Jr. | 210/198.2 |
| 4,871,431 | 10/1989 | Parsi | 204/301 |
| 4,880,513 | 11/1989 | Davis et al. | 204/301 |
| 4,925,541 | 5/1990 | Giuffrida et al. | 204/301 |
| 4,969,983 | 11/1990 | Parsi | 204/182.4 |

Primary Examiner—Stan Silverman
Assistant Examiner—Cynthia L. Nessler
Attorney, Agent, or Firm—Flehr, Hohbach, Test, Albritton & Herbert

[57] ABSTRACT

A method and apparatus has been provided for generating a high purity aqueous stream with selected ionic species—either cation (e.g. sodium) or anion (e.g. sulfate) and suitable for use as a chromatography eluent. In one form, an eluent generating means defines a source channel and a product channel separated by a permselective ion exchange membrane including exchangeable ions of the same charge as the selected ionic species. The membrane allows passage of ions of the same charge as the ionic species but is resistant to transmembrane passage of ions of opposite charge. Means is provided for applying an electrical potential between the source channel and product channel. In another form of the device, two different membranes define two source channels, a positively charged, anode source channel and a negatively charged cathode source channel, and a product channel. The effluent from the product channel is directed to the chromatographic separation means. Means is also provided for supplying liquid sample to the chromatographic separation means.

32 Claims, 6 Drawing Sheets

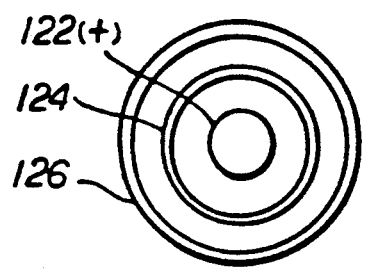
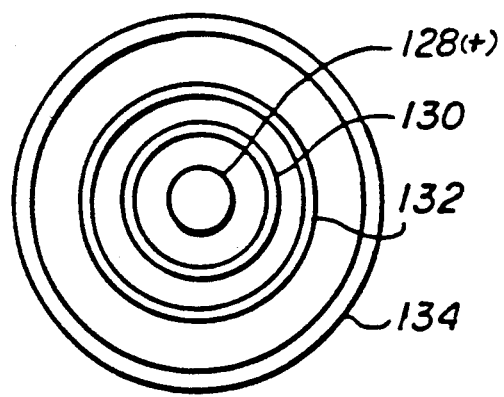
Fig. 8 Fig. 9
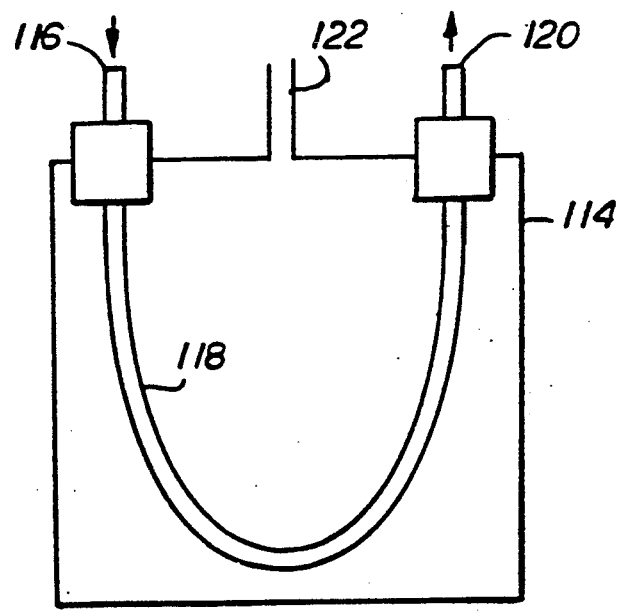
Fig. 7

METHOD AND APPARATUS FOR GENERATING A HIGH PURITY CHROMATOGRAPHY ELUENT

BACKGROUND OF THE INVENTION

The present invention relates to a method and apparatus for the generation of a high purity chromatography eluent, particularly a gradient eluent.

In practicing liquid chromatography, a sample containing multiple components is directed through a chromatography medium contained typically in an ion exchange resin bed. The components are separated on elution from the bed in a solution of eluent.

One effective form of liquid chromatography is referred to as ion chromatography. In this known technique, the ions in the sample solution are directed through a chromatographic separation stage using such eluent containing an electrolyte and thereafter to a suppression stage, followed by detection, typically by an electrical conductivity detector. In the suppression stage, the electrical conductivity of the electrolyte is suppressed but not that of the separated ions so that the latter may be detected by a conductivity cell. This technique is described in detail in U.S. Pat. Nos. 3,897,213, 3,920,397, 3,925,019 and 3,956,559.

Suppression or stripping of the electrolyte by an ion exchange resin bed is described in the prior art references. A different form of suppressor is described in EPA Pub. No. 32,770 published July 29, 1981. Here, an ion exchange membrane in the form of a fiber or sheet is used in place of the resin bed. In the sheet form, the sample and eluent are passed on one side of the sheet and a flowing regenerant is passed on the other side of the sheet. The sheet is in the form of an ion exchange membrane partitioning regenerant from the effluent of chromatographic separation. The membrane passes ions of the same charge as the exchangeable ions of the membrane to convert the electrolyte of the eluent to weakly ionized form, followed by detection of the ions.

An improved membrane suppressor device is disclosed in EPA Pub. No. 75,371, published Mar. 30, 1983. There, a hollow fiber suppressor is packed with polymer beads to reduce band spreading. There is a suggestion that such packing may be used with other membrane forms. Furthermore, there is a suggestion that the function of the fiber suppressor is improved by using ion exchanger packing beads. No theory is set forth as to why such particles would function in an improved manner.

Another suppression system is disclosed in EPA Pub. No. 69,285, published Jan. 12, 1983. There, the effluent from a chromatographic column is passed through a central flow channel defined by flat membranes on both sides of the channel. On the opposite sides of both membranes are regenerant channels through which the regenerant solutions are passed. As with the fiber suppressor, the flat membranes pass ions of the same charge as the exchangeable ions of the membrane. An electric field is passed between electrodes on opposite sides of the effluent channel which is stated to increase the rate of suppression. One problem with this electrodialytic membrane suppressor (EDS) system is that very high voltages (50-500 volts DC) are required. As the liquid stream becomes deionized, electrical resistance increases, resulting in substantial heat production. Such heat is detrimental to effective detection because it greatly increases noise and decreases sensitivity. Another problem is that the system generates excessive quantities of hydrogen gas.

An improved form of suppressor is described in EPA Pub. No. 180,321, published May 7, 1986. In this apparatus, the suppressor includes at least one regenerant compartment and one effluent compartment separated by an ion exchange membrane sheet. The sheet allows transmembrane passage of ions of the same charge as its exchangeable ions. Ion exchange screens are used in the regenerant and effluent compartments. Flow from the effluent compartment is directed to a detector, such as an electrical conductivity detector, for detecting the resolved ionic species. The screens provide ion exchange sites and serve to provide site to site transfer paths across the effluent flow channel. A sandwich suppressor is also disclosed including, a second membrane sheet opposite to the first membrane sheet and defining a second regenerant compartment. Spaced electrodes are disclosed in communication with both regenerant chambers along the length of the suppressor. By applying an electrical potential across the electrodes, there is an increase in the suppression capacity of the device.

Another EDS is disclosed in U.S. Pat. No. 4,403,039. An anode is disposed in the center of a tubular ion exchange membrane surrounded by a concentric annular flow channel and a tubular cathode.

An electrolytic membrane suppressor (EMS) is disclosed in Strong, D.L.; Dasgupta, P.K.: Anal. Chem. 1989, 61 939-945. That paper discloses single and double membranes in concentric tubular form. In the eluent which is suppressed, sodium ion passes to an annular regenerant solution container fed with water so that the effluent from such regenerant chamber is sodium hydroxide.

There is a general need for high purity eluents for liquid chromatography and a particular need in ion chromatography. Similarly, there is a need for a convenient way to generate gradient eluents of precise concentrations and timing. Gradient eluents are eluents at different strengths and concentrations used during the course of a single chromatography run. The use of gradient eluents for ion chromatography is described in Rocklin, R.D., et al. *J. of Chromatographic Science*, Vol. 27, p. 474, Aug. 1989; Qi, D., et al. *Analytical Chemistry*, Vol. 61, p. 1383, 1989; and Shintani, H., et al., *Analytical Chemistry*, Vol. 59, p. 802, 1987.

SUMMARY OF THE INVENTION

In accordance with the present invention, a method and apparatus has been provided for generating a high purity aqueous stream with selected ionic species-either either cation (e.g. sodium) or anion (e.g. sulfate) and suitable for use as a chromatography eluent. In one form, an eluent generating means defines a source channel and a product channel separated by a permselective ion exchange membrane including exchangeable ions of the same charge as the selected ionic species. The membrane allows passage of ions of the same charge as the ionic species but resistant to transmembrane passage of ions of opposite charge. Means is provided for applying an electrical potential between the source channel and product channel. The effluent from the product channel is directed to chromatographic separation means. Means is also provided for supplying liquid sample to the chromatographic separation means.

It is apparent that by using this system, only ions of the same charge as the selected ionic species flow across the ion exchange membrane into the product stream since the membrane is resistant to transmembrane passage of ions of the opposite charge. This eliminates such oppositely charged ions which would otherwise interfere with the accurate analysis of the ionic constituents of the sample during ion chromatography.

In the above single membrane device, gas is electrolytically generated in the product channel. For example, where sodium is the selected ionic species, the membrane is a cation exchange membrane and allows the passage of positively charged ions only. The anode-source channel is positively charged and the product channel is negatively charged. In the product channel, water is electrolyzed to provide a source of hydroxide ion for the sodium which diffuses across the membrane. Such electrolysis also generates hydrogen gas. The presence of such gas in the product channel can be detrimental to accurate chromatographic analysis. Means is provided for removing such gas from the product prior to use in chromatography. In one such means, gas is removed from the product by passing it through a tube of hydrophobic gas diffusion membrane. This tube functions to permit the ready passage of gas but substantially prevents the transmembrane passage of liquid.

In another form of the device, two different membranes define two source channels, a positively charged, anode source channel and a negatively charged cathode source channel, and a product channel. For example, where sodium is the selected ionic species, the first membrane is a cation exchange membrane and is adjacent to the anode source channel. Hydroxide in the anode source channel is oxidized and sodium ion passes across the cation membrane into the product channel. Oxygen gas produced by the anodic process substantially remains in the anode source channel. The second membrane, an anion exchange membrane adjacent to the cathode source channel, allows the passage of negatively charged ions but substantially blocks positively charged ions. The cathode source channel is negatively charged. Water in the second source channel is reduced to hydroxide ion and hydrogen gas and hydroxide ion passes across the anion exchange membrane into the product channel. Hydrogen gas produced by the cathodic process substantially remains in the cathode source channel. Thus, largely gas-free sodium hydroxide is produced in the product channel.

In a preferred embodiment, the electrical current flowing between the source channel(s) and product channel is systematically varied by prior programming to correspondingly vary the concentration of the selected ionic species in the product stream. Thus, this unit renders the device particularly effective for use as a gradient eluent generator.

BRIEF DESCRIPTION OF THE DRAWINGS

FIGS. 6 and 7 are side schematic views of gas removal device according to the invention.

FIGS. 8 and 9 are a schematic cross sectional view of two different tubular forms of electrolytic cell.

DETAILED DESCRIPTION OF THE PREFERRED EMBODIMENTS

The eluent generating means of the present invention will first be described in combination with ion chromatographic apparatus to which the eluent product is directed. For that purpose, for the analysis of anions on a chromatographic separation means, the eluent is an electrolyte, typically a cation hydroxide such as sodium hydroxide. Conversely, for the analysis of cations, the eluent typically is an acid such as hydrochloric acid. However, the eluent generating system of the present invention is also applicable to liquid chromatography forms other than ion chromatography. For example, it is applicable to liquid chromatography using an ultraviolet detector. In such instance, the eluent may be in other than an acid or base form, e.g. a salt such as KCl, $KClO_4$, $KNO_3$ or the corresponding sodium salts.

Figure 1:
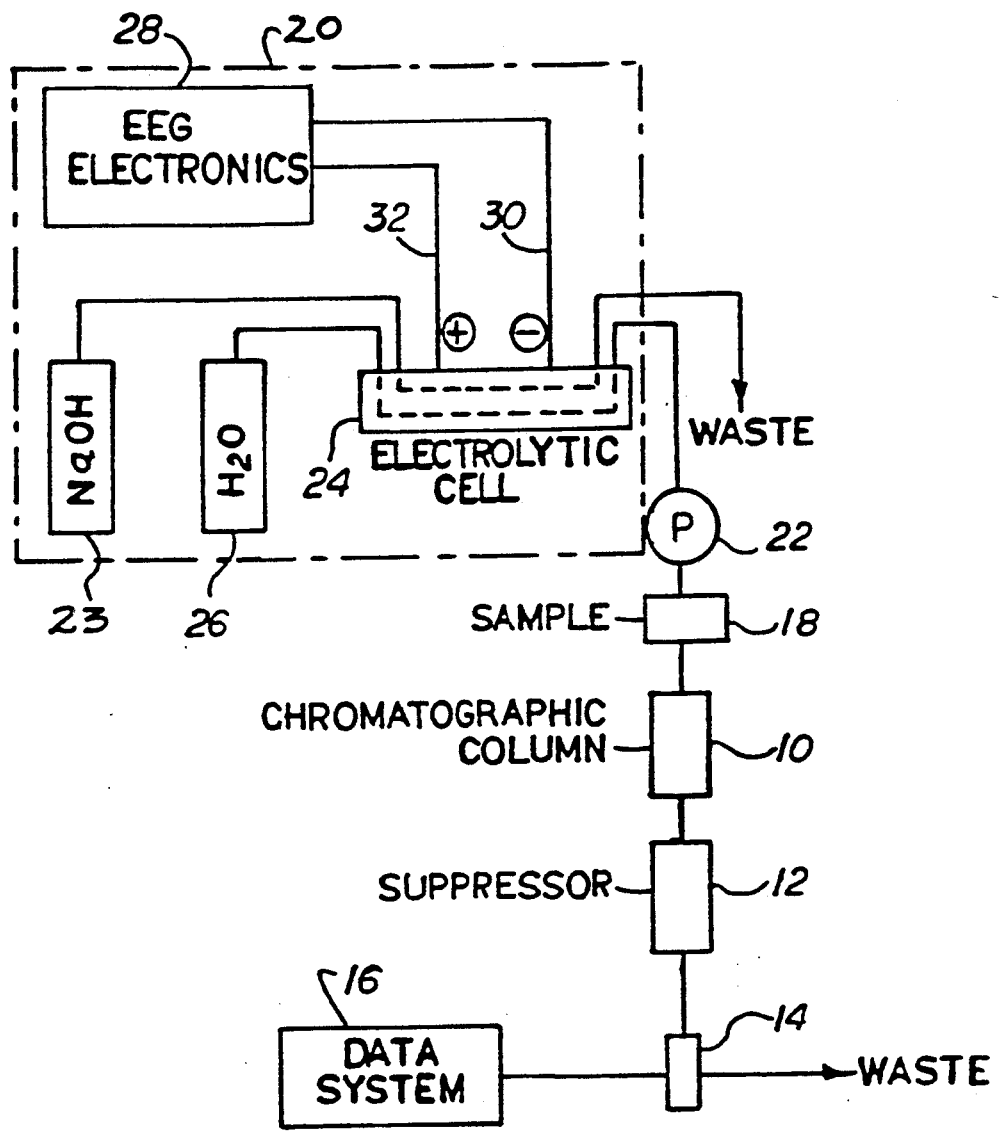
FIG. 1 is a schematic view of apparatus according to the invention for generating eluent and using it to perform ion chromatography.

Referring specifically to FIG. 1, a simplified ion chromatography apparatus is illustrated. The system includes chromatographic separation means, in the form of a chromatographic column 10, which is packed with chromatographic separation medium. In one embodiment, such medium is in the form of ion exchange resin. In another embodiment, the separation medium is a porous hydrophobic chromatographic resin with essentially no permanently attached ion-exchange sites. Such chromatography systems are described in EPA Publication 180,321, incorporated herein by reference.

Suppressor means 11 is in series with column 10 serving to suppress the conductivity of the eluent electrolyte in the effluent of column 10 but not the conductivity of the separated ions.

The effluent from suppressor means 12 is directed through a flow-through conductivity cell 14 for detecting the resolved ionic species in the sample in the effluent from suppressor means 12. A suitable data system is provided in the form of a conventional conductivity detector 16 for measuring the effluent from suppressor means 12 in conductivity cell 14. The effluent thereafter flows to waste. A suitable sample is supplied through sample injection valve 18. Eluent from an eluent generator generally designated by the number 20 is directed by pump 22 to chromatographic column 10.

The solution leaving chromatographic column 10 is directed to suppressor means 12 wherein the eluent is converted to a weakly conducting form. The effluent with separated ionic species then passes through conductivity cell 14.

In conductivity cell 14, the presence of ionic species produces an electrical signal proportional to the amount of ionic material. Such signal is typically directed from cell 12 to a conductivity meter forming part of data system 16, thus permitting direct detection of the concentration of the separated ionic species.

The system of FIG. 1 is illustrated in the form of a system useful for anion analysis. Here, the selected ionic species of the eluent is sodium which is directed from a source 23 of sodium in hydroxide form to a anode-source flow channel of electrolytic cell 24. A product channel is fed from a container 26 of an aqueous product liquid (e.g. water) to the opposite side of an ion exchange membrane which separates the flow of the source sodium hydroxide from the water as will be described hereinafter. Suitable electronics 28 is provided for generating a current between cathode 30 and anode 32 disposed on opposite sides of the membrane as will be described below.

Figure 2:
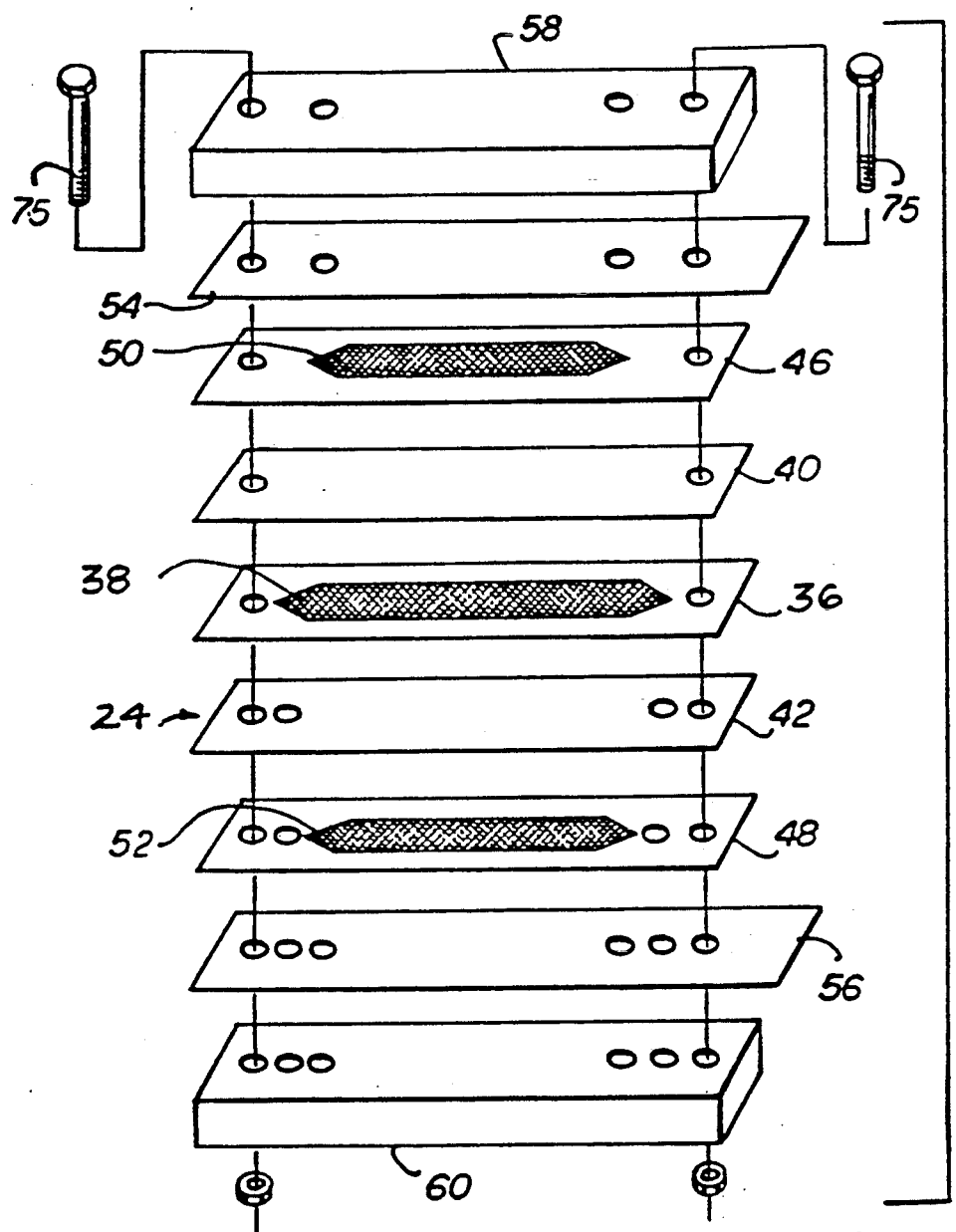
FIG. 2 is an exploded view of the electrolytic cell device including two source channels, on either side of an eluent product channel, each including a screen.
Figure 3:
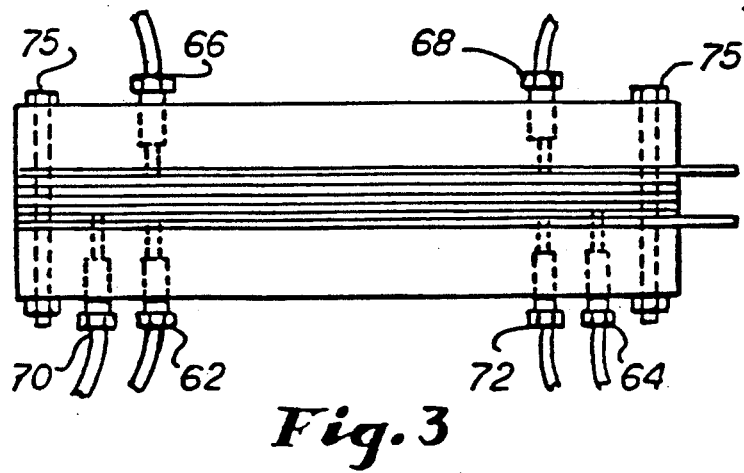
FIG. 3 is a side elevational view of an eluent generating means according to the invention.
Figure 5:
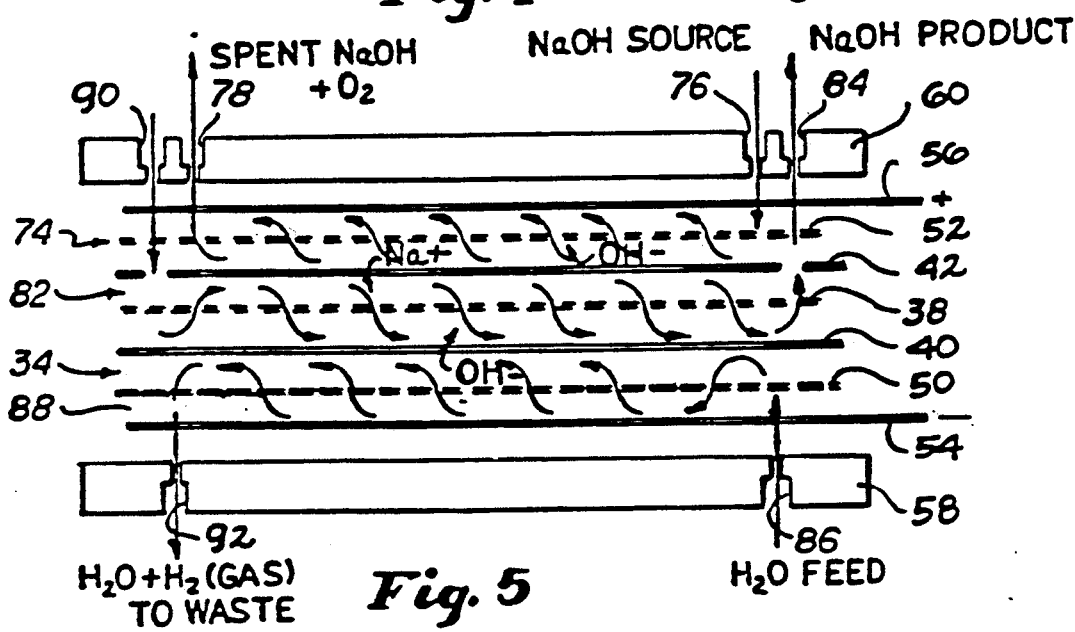

Referring to FIGS. 2, 3 and 5, an electrolytic cell generally designated by the number 24 is illustrated in the form of a sandwich electrolytic cell including three flow channels. Referring specifically to FIGS. 2 and 3, cell 24 includes a central product channel flanked by two source channels on either side. Each source channel also contains an electrode. The cathode source channel is supplied with water and is the source of hydroxide (produced electrolytically) and is separated from the product channel by an anion exchange membrane. The anode source channel is supplied with source sodium hydroxide and is separated from the product channel by a cation exchange membrane. Both source channels also act as gas carrier channels to direct electrolytically produced oxygen and hydrogen gas to waste. The ion exchange membranes substantially prevent the gases from entering the product stream. Cell 24 includes means defining a product flow channel partially bounded by gasket 36 defining a central cavity. To minimize dead space in the cavity it is preferable to form both ends of the cavities in a peak or V-shape.

It is preferable to include ion exchange means in the cavity. In one preferred form of the invention, such means is in the form of a screen 38, to be described more fully below. Alternatively, ion exchange particles may be disposed in the cavity.

Referring to FIGS. 2 and 3, ion exchange membrane sheets 40 and 42 are mounted to extend along opposite sides of screen 38 and, together with gasket 36, define the outer perimeter of the product flow channel. Openings are provided for the product liquid inlet (e.g. water from source 26) and outlet to the line for chromatographic column 10. Source channel gasket 46 and gasket 48 are in contact with the facing surfaces of membrane sheets 40 and 42, respectively, and together define two source channels. These screens provide ion paths of the type described in EPA 180,321. Ion exchange means also are suitably provided in both of such channels, preferably in the form of ion exchange screens 50 and 52 respectively. Openings are provided for inlet and outlet flow through gasket 48.

As illustrated, wire mesh electrodes 54 and 56 are mounted to the exterior sides of screens 50 and 52, respectively, across which a direct electric current is applied as through preprogrammed electronics 28 in a manner to be described hereinafter. Suitable electrodes are formed of rhodium, stainless steel, platinum, gold, or carbon. In an alternative to separate electrodes and screens, the screens may be formed of metal and used as the electrodes. Such electrodes also include openings to permit inlet and outlet flow of solution.

External blocks 58 and 60 are formed of a rigid nonconductive material such as polymethylmethacrylate or polyetherether ketone (PEEK) and serve to provide structural support for the remainder of device 24. Referring to FIG. 3, fittings 66 and 68 are provided for source liquid inlet and outlet lines to and from the source channel. Similarly, fittings 64 and 70 are provided for product liquid supply to and from the product channel. Similarly, fitting 62 and 72 are provided inlet and outlet lines for fluid, (e.g. water) to and from the other source channel.

The above assembled sheets and gaskets are mounted under pressure which is supplied by bolts 75 to form liquid tight seals. It is preferable for maximum ion transfer across the membranes to connect the lines to the flow channels for countercurrent flow.

Gasket 36 may be formed of any suitable material which provides a liquid seal for the product flow channel which it defines. A suitable material for the gasket is a flexible liquid silicone-based rubber such as supplied under the name RTV ® by General Electric Co. or a plastic sheet such as Parafilm ® supplied by American Can Co. A similar material may be used for gaskets 46 and 48.

Ion exchange membrane sheets 40 and 42 may be of a type such as disclosed in Slingsby, et al. U.S. Pat. No. 4,486,312, dated Dec. 4, 1984. In particular, such sheets may be cation-exchange or anion-exchange membranes with polyethylene, polypropylene, polyethylenevinylacetate-based substrates. Other suitable substrates include polyvinylchloride or polyfluorocarbon-based materials.

The substrate polymer is solvent and acid or base resistant. Such substrates are first grafted with suitable monomer for later functionalizing. Applicable monomers include styrene and alkylstyrenes such as 4-methylstyrene, vinylbenzylchloride or vinylsulfonates, vinylpyridine and alkylvinylpyridines. As an example, to form a cation exchange membrane, the sheets grafted with styrene monomers are functionalized suitably with chlorosulfonic acid, sulfuric acid, or other $SO_2$ or $SO_3$· sources. To form an anion exchange membrane, the sheets grafted with vinylbenzylchloride monomers are functionalized with alkyl tertiary amines such as trimethylamine or tertiary alkanolamines, such as dimethylethanolamine. Particularly effective membranes are no more than 10 mil thick, and preferably no more than 2-4 mil. Suitable polyethylene substrate membranes of the foregoing type are provided by RAI Research Corp., Hauppauge, N.Y. (the cation exchange membrane provided under designation R5010 (0.008 in. thick) and the anion exchange membrane under designation R4015 (0.004 in. thick)). Other cation exchange membranes supplied by the same company which are fluorocarbon based include R1010 (0.002 in. thick) and R4010 (0.004 in. thick). Other suitable commercially available membranes include ion exchange membranes produced under the trade name Selemion ®, such as Selemion CMV and Selemion AMV, and ion exchange membranes produced under the trade name Nafion ®, such as Nafion 117 and the Nafion series 100, 300, 400 and 900.

Screens 38, 50 and 52 may be formed integral with the effluent gaskets or inserted independently into the effluent flow channel. Details regarding suitable screens are disclosed in EPA Publication 180,321. In that regard, the structure of the cell 24 may be of the same type as the one illustrated in FIG. 2 of EPA Publication 180,321. The effluent flow channel and two regenerant flow channels correspond to the product flow channel and two source flow channels of the present invention.

FIG. 5 schematically illustrates an electrolytic cell for generating pure sodium hydroxide. In this instance, the source liquid comprises sodium hydroxide which is directed to anode-source channel 74 through port 76. The sodium hydroxide solution passes from right to left as illustrated along screen 52 and exits at port 78. Product feed liquid, in this instance water, flows countercurrent to the source liquid. The water is directed through inlet port 90 into product channel 82 where it flows along screen 38 and exits through product outlet port 84, suitably for supply as an eluent to a chromatography column. In FIG. 5 a cathode source liquid (water) flows countercurrent to the product feed liquid. It is directed through inlet port 86 and flows along screen 50 in source channel 88 and flows along screen 50 to outlet port 92 where it flows to waste.

In the above system for generating sodium hydroxide, electrode 56 is an anode and electrode 54 is a cathode. Membrane 42 is a cation exchange membrane while membrane 40 is an anion exchange membrane. Preferably, screens 38 and 52 are cation screens while screen 50 is an anion screen. In operation, the water is hydrolyzed in the anode source channel generating oxygen according to the following equations:

$$6H_2O \rightarrow 4H_3O^+ + O_2(g) + 4e^- (+2.4v) \quad (1)$$

$$4OH^- \rightarrow 2H_2O + O_2(g) + 4e^- (+0.4v) \quad (2)$$

For NaOH solutions, equation 2 is the dominant reaction.

The sodium ion in the source liquid passes through cation exchange membrane 42 while hydroxide is substantially excluded from transmembrane passage by Donnan exclusion. The spent sodium hydroxide and oxygen generated in source channel 74 is passed to waste.

In the cathode source channel 88, hydroxide and hydrogen gas are generated according to the following equation:

$$2e^- + 2H_2O \rightarrow 2OH^- + H_2(g)(-0.83v) \quad (3)$$

The hydroxide generated at cathode 54 is passed through anion exchange membrane 40 into product channel where it combines with the sodium ion which is passed across membrane 42 to form the sodium hydroxide product stream exiting port 84. While the sodium is driven across cation exchange membrane 42 under the potential applied between cathode 54 and anode 56, it is impeded from passage through anion exchange membrane 40 into cathode source channel 88 by Donnan exclusion.

One advantage of the above system is that hydrogen gas generated at cathode 54 does not substantially pass through ion exchange membrane 40 but, instead, is removed in the waste stream exiting port 92. If not removed, such hydrogen gas in the chromatography eluent would interfere with detection of the components of the sample stream after chromatographic separation.

A major advantage of this system is that the concentration of the sodium in the product channel can be varied as desired by adjusting the current applied between cathode 54 and anode 56. This is particularly effective for forming a gradient eluent in which such eluent concentrations are varied during the course of a run. The ability to reproducibly supply precisely varied concentrations in a gradient eluent based on a single eluent source is particularly advantageous to form a compact automated chromatography instrument.

Another advantage of the system is the high purities which can be obtained by use of the present system, particularly for ion chromatography. As discussed, only the cation from the sodium hydroxide source fed at port 76 passes through membrane 42 while the anions in the solution are impeded or prevented from such transmembrane passage. Cation (sodium) hydroxide is used as an eluent for anion analysis. Thus, the contaminants of most concern are anions present in the sodium hydroxide source. Since membrane 42 passes cations but excludes anions, the sodium hydroxide product stream is purified of such potentially interfering anion contaminants. By supplying highly purified water to the product and cathode source channel, an eluent of exceptional purity is formed.

Sodium hydroxide has been illustrated as the selected ionic species in hydroxide form for use as the source and ultimate product. However, other cations useful for chromatography may also be employed, including lithium, potassium, rubidium, cesium, ammonium, and tetralkyl ammonium.

The above system has been described with respect to the formation of sodium hydroxide for anion analysis. It should be understood that the system is readily adapted to production of an acid, such as hydrochloric acid, for cation analysis, by supplying NaCl or HCl to the cathode source channel, deionized water to the anode source channel and ultrapure water to the inlet of the product stream.

By the above adjustments, chloride ion passes through anion exchange membrane 40 while electrolytically generated hydronium ion passes through cation exchange membrane 42. These ions form hydrochloric acid in the product stream which passes through product port 84. Oxygen is generated in the anode source channel 74 and passes to waste through port 78. Similarly, hydrogen generated in cathode source channel 88 passes to waste through port 92.

Referring again to sodium hydroxide as the produced eluent, the passage of the sodium across membrane 42 is significantly assisted by the application of a potential across electrodes 54 and 56. The potential difference is at its greatest between anode source channel 74 and cathode source channel 88. However, there is also a potential differential between anode source channel 74 and product channel 82 and between product channel 82 and cathode source channel 88. As defined herein, reference to "applying an electrical potential across channels" includes any potential existing in intermediate channels provided by applying a potential to electrodes external to such channels. In other words, reference to applying an electrical potential across source channel and product channel includes the application of any potential that accomplishes a difference in potential between those two channels even though the electrodes are in channels remote from them such as illustrated in FIG. 5.

In one important aspect of the present invention, the electrical current is systematically varied to vary the concentration of the selected ion species (e.g. sodium) in the product stream thereby providing a convenient source of gradient eluent. A programmable electronic device is used to control the application of the current to provide precise concentrations of eluent at timed intervals. One suitable device is Hewlett-Packard Model 6289A constant current power supply controlled by an IBM PC-type computer with a Metrabyte Model DAC-02 digital to analog voltage converter.

Figure 4:
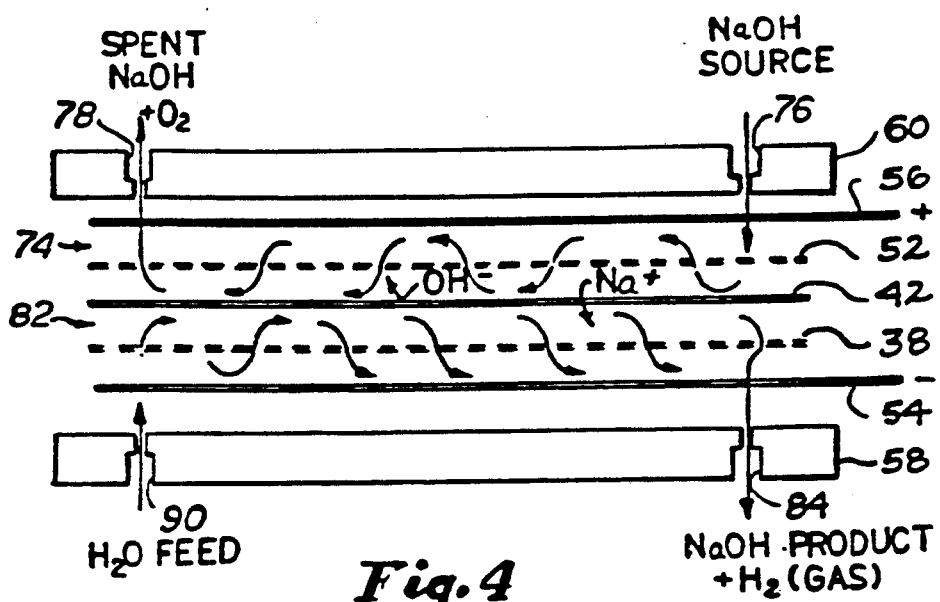
FIGS. 4 and 5 are schematic side cross-sectional views of single and double membrane eluent generating devices, respectively, according to the present invention.

Referring to FIG. 4, a simplified version of the electrolytic cell of the present invention is illustrated with only an anode source flow channel 74 and a product flow channel 82. In essence, this device is substantially the same as the device of FIG. 5 with the exception that membrane 40 is eliminated together with screen 50. Again, assuming the feed of a cation hydroxide (sodium hydroxide) for use as the ultimate product, electrode 56 is an anode and electrode 54 a cathode, while membrane 42 is a cation exchange membrane and screens 38 and 52 are cation exchange screens.

Referring to the single membrane system of FIG. 4, the reactions of equations (1) and (2) still occur in anode source channel 74 so that spent sodium hydroxide and oxygen gas exit through port 78. Similarly, the reaction of equation (3) occurs in the product channel. The advantage of this configuration is high faradaic efficiency, i.e., efficient use of the electrical energy to achieve the desired electrochemical production of sodium hydroxide. Additionally, this configuration generally displays the lowest electrical resistance and therefore the lowest Joule heating. One disadvantage of this simplified system is that electrolytically generated gas, hydrogen in this instance, passes through port 84 as the product stream. For optimum use as an eluent, it is desirable to remove the hydrogen gas prior to injection into the chromatography column.

Figure 6:
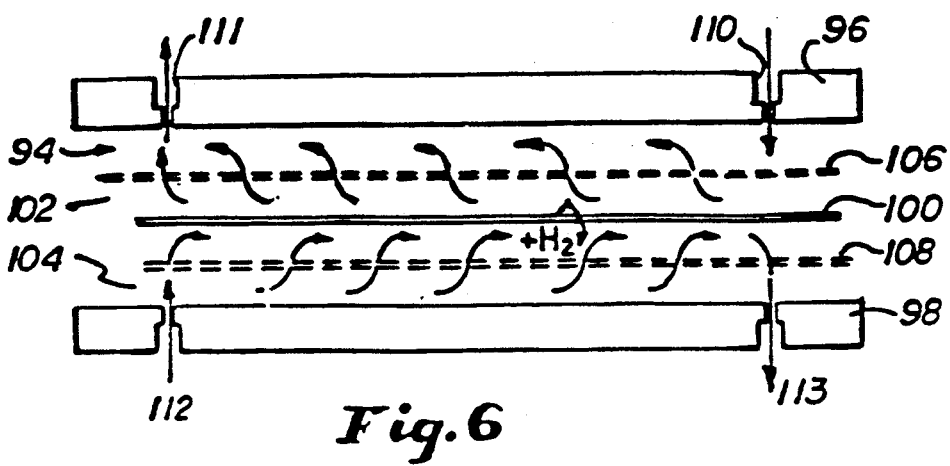

Referring to FIG. 6, one system for hydrogen gas removal from the product stream is illustrated as gas diffusion cell 94 which is structurally similar to the electrolytic cell of FIG. 4. Cell 94 is defined by blocks 96 and 98 and contains a gas diffusion membrane 100 separating a degassed product channel 102 from a gas carrier channel 104. Neutral screens 106 and 108 may be provided as support for membrane 100. Membrane 100 functions to permit the ready transmembrane passage of gas in the sodium hydroxide exiting from port 84 of FIG. 4 but substantially preventing the transmembrane passage of liquid. In this manner, the product exiting port 111 is substantially free of the hydrogen gas. For this purpose, a suitable membrane is a hydrophobic gas diffusion membrane such as ones sold under the trademarks Accurel ® or Celgard ® or Gortex ®.

Referring to FIG. 7, an alternative device 114 is illustrated for removing gas (e.g. hydrogen) generated in the electrolytic cell from the product stream (e.g. sodium hydroxide). Such gas-containing product is directed through port 116 into a porous hydrophobic tube 118 which is configured for the product to flow downwardly and then upwardly out port 120. The tube 118 may be formed of similar hydrophobic materials (e.g. as porous (expanded) PTFE, Accurel ® or Celgard ®) to the membrane of FIG. 6. The hydrogen gas flows outwardly through tube 118 to a gas vent 122.

Another form of the electrolytic cell takes advantage of the lower electrical resistance and higher stability of cation exchange membranes relative to anion exchange membranes presently available. The device is of the same configuration as that of FIG. 5. However, in this instance, both membranes 40 and 42 are cation exchange membranes. Also, a restrictor membrane, not shown, is layered below membrane 40 in the cathode source channel. Because sodium ion can pass through both membranes 40 and 42, NaOH quickly builds up in the cathode source channel. This allows high concentrations of NaOH to be formed locally. Note that this NaOH is electrolytically formed and is devoid of any anions other than hydroxide. The high concentration of hydroxide overcomes the Donnan barrier which forbids the passage of a negatively charged ion through a cation exchange membrane and allows passage of OH$^-$ through 40 into the product channel. In other words, the build-up of sodium hydroxide below 40 allows 40 to function as a membrane which permits OH$^-$ to pass through. Because of the restrictor membrane, the passage of sodium ion is impeded through 40 relative to 42, significant amounts of NaOH are formed in the product channel. It is suitably formed of a perforated (e.g., by holes on the order of 0.7 mm diameter) Teflon plate (e.g. 0.25 mm thick).

When electric potential is applied, sodium ion migrates from the product channel 74 through membrane 42. Because of the restrictor membrane, as detailed above, hydroxide passes from the cathode source channel 88 into the product channel thereby forming sodium hydroxide in the product channel. Membranes 42 and 40 serve to isolate electrolytically produced gasses from product channel 82. Other restrictor membranes may be employed in place of Teflon plates (e.g. dialysis membranes and filter sheets).

FIG. 8 is a schematic cross-sectional view of a tubular form of electrolytic cell according to the invention. In this instance, it is assumed that the anode source channel is the lumen of the innermost tube. The device includes anode 122 (in the form of a rod or wire, e.g., formed of platinum, gold, carbon or stainless steel), cation exchange membrane 124 and outer wall 126 which may be formed of conductive material to serve as the cathode. If desired, ion exchange resin may be disposed in the source and product channels. This system is comparable in general function to the one illustrated in FIG. 4. Alternatively, the product channel may be the lumen of the inner tube. In this instance, the polarities of the electrodes are reversed. Membrane 124 may be formed of stretched or unstretched tubular ion exchange membranes, e.g., Nafion 811X from Perma-Pure Products, N.J. Outer wall 126 may be formed of a 18 ga. stainless steel (SS) tubular case.

FIG. 9 illustrates a tubular type of dual membrane device. It is generally constructed by inserting a length of suitably inert wire inner electrode 128 into a length of tubular inner membrane 130 which is itself inserted inside a length of somewhat larger diameter tubular outer membrane 132 and enclosing the whole assembly in a stainless steel tube 134 of appropriate dimensions. The outer tube itself functions as the electrode, connections being made at the ends to allow access to the flow channels between the inner electrode and inner membrane, between the two membranes (annulus) and between the outer membrane and stainless steel case.

The foregoing description has been of an eluent generator for ion chromatography. Thus, for anion analysis, the product is the cation hydroxide, typically sodium hydroxide, while for cation analysis the eluent is an acid such as hydrochloric acid. However, it should be understood that the system may also be employed to produce high purity salts at varying concentrations. Such salts, could be used as gradient eluents for other forms of liquid chromatography. Thus, for example the sample solution could be separated on the chromatography column and passed directly to an ultraviolet detector.

In this application, a dual membrane cell using one anion exchange and one cation exchange membrane could be used. A salt or base solution of the selected cation would be fed to the anode source channel and a solution of the acid or salt form of the selected anion would be fed to the cathode source channel. The selected anion would permeate to the product channel across the anion exchange membrane, the selected cation would permeate across the cation exchange membrane into the product stream, thereby forming the desired salt solution. The concentration of the desired salt solution is determined by the magnitude of the applied electrical current.

In order to illustrate the present invention, the following examples of its practice are provided.

EXAMPLE 1

Eluent Generator with Two Channels, One Cation Exchange Membrane and Planar Geometry In this demonstration, an eluent generator with an anode-source channel and a product channel was used. The channels were separated by a cation exchange membrane. The device had planar geometry of the type generally illustrated in FIG. 4.

The eluent generator was constructed as follows. Cation exchange screens with integral gaskets were prepared as described by EPA Pub. No. 180,321, published May 7, 1989. A single-screen channel/electrode sub-assembly was made by attaching pieces of platinum wire gauze onto a gasketed screen and connecting them together with platinum wire. Wire gauze was 52 mesh woven from 0.1 mm diameter wire. A double-screen channel/electrode subassembly was made by laying another gasketed screen upon a single-screen channel/electrode sub-assembly and sandwiching the wire mesh between the two gasketed screens. Sub-assemblies were stacked: double-screen channel/electrode sub-assembly on a Selemion CMV cation exchange membrane on a single-screen channel/electrode sub-assembly. The stack was clamped together in a plastic housing as shown in FIG. 4.

The components functioned as follows. The double-screen channel/electrode sub-assembly comprised the anode-source channel and contained the anode. The Selemion CMV cation exchange membrane separated the anode-source and product channels. The single-screen channel/electrode sub-assembly comprised the product channel and contained the cathode.

The following external connections were made. The anode-source channel was fed with 250 mM sodium hydroxide at about 5 ml/min, and its effluent was directed to waste. The product channel fed with deionized water at about 1 ml/min, and its effluent (the "product") was directed to a gas-removal device and then to chromatography instrumentation. The anode and cathode were connected to the positive end negative terminals, respectively, of the constant-current power supply previously described.

The following processes occurred in the eluent generator. In the anode-source channel, sodium hydroxide was oxidized according to the reaction:

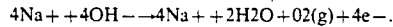

Sodium ions in the anode-source channel passed across the cation membrane into the product channel to carry the current. In the product channel water was reduced according to the reaction:

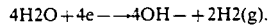

Hydroxide ions thus created, along with sodium ions from the anode-source channel, formed sodium hydroxide product in the product channel. Purity of the sodium hydroxide product depended on the quality of the feed water and the ability of the membrane to exclude contaminants found in the sodium hydroxide feed.

Results were as follows. When the current was 59. mA and the voltage was 2.66 VDC, the device generated 38 mM sodium hydroxide at about 1 ml/min. When conditions were 91 mA and 3.08 VDC, it generated 59 mM sodium hydroxide at about 1 ml/min. When conditions were 151 mA and 3.84 VDC, it generated 98 mM sodium hydroxide at 1 ml/min.

EXAMPLE 2

Chromatography

Figure 10:
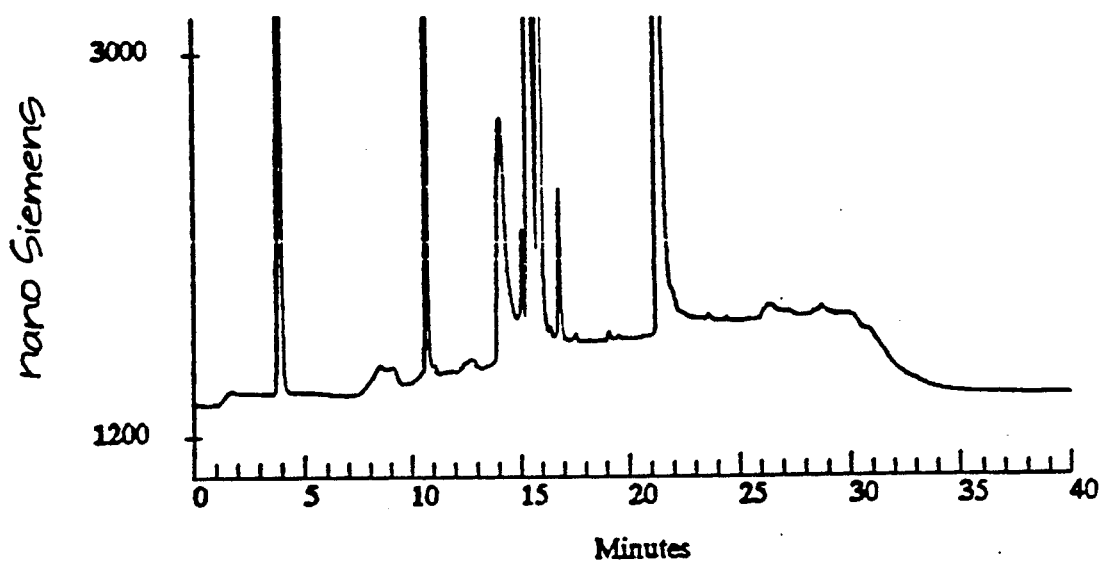
Figure 11:
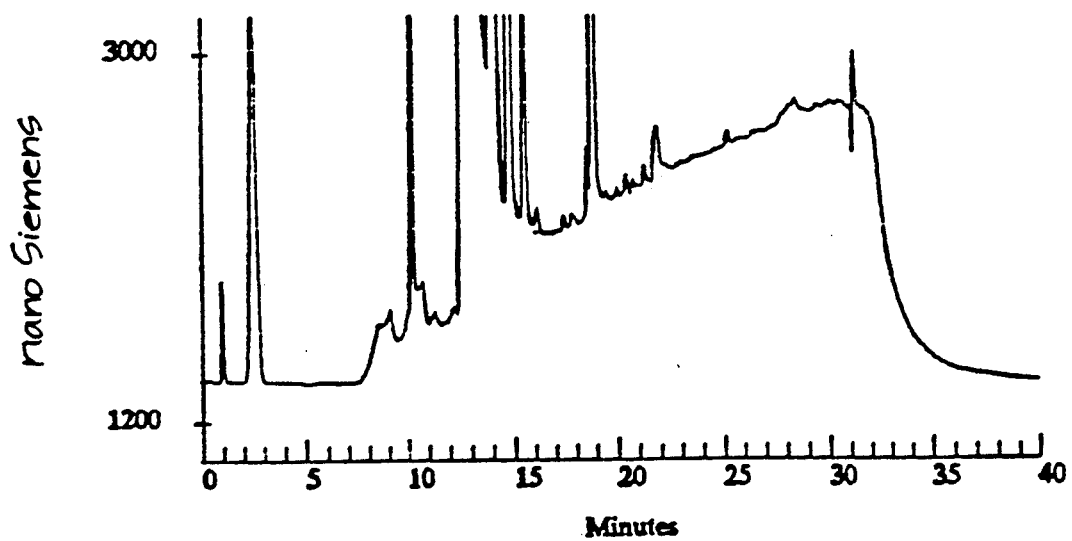

The chromatographic system used to generate the chromatograms in FIGS. 10 and 11 was a Dionex 4500i ion chromatograph, Dionex Corporation, Sunnyvale, Calif. For FIG. 10, the product stream from an eluent generator cell as described in Example 1 was connected to the inlet of the pump, by-passing all of the low pressure gradient mechanics such that a change in eluent concentration could only be caused by a change in applied current to the EEG cell. The applied current to the cell is from an HP6289A controlled by a Metrabyte DAC board mounted in an IBM compatible computer. A basic program was written to supply a constant rate of change in voltage from the Metrabyte DAC board to the HP6289A, which results in a constant rate of change in current applied to the eluent generator cell which results in a constant rate of change in product stream concentration. FIG. 10 represents a chromatogram generated as a result of a gradient from approximately 1 mM to 90 mM NaOH generated in this way. The column is a Dionex HPICAS5A. The eluent is flowing at a constant 1 ml/min., the injection volume is 10 μl. The sample injected is fluoride 2 ppm, chloride 3 ppm, nitrate 10 ppm, phosphate 15 ppm, sulfate 15 ppm. Note that the background change during the course of the gradient (0–30 minutes) is approximately 0.5 μS.

FIG. 11 is a chromatogram generated on the same instrument, without using an eluent generator cell, in its normal gradient configuration. Eluent 1 is 1 mM NaOH. Eluent 2 is 200 mM NaOH. The gradient is 100% Eluent 1 to 55% Eluent 1, 45% Eluent 2 in 30 minutes. Note that the baseline shift during the course of the gradient is approximately 2 μS, or four times greater than the gradient using the eluent generator cell. The background shift for the standard configuration is typical as described in Shintani, H. et al., (1987), *Analytical Chemistry*, 59, p. 802.

EXAMPLE 3

Eluent Generator with Three Channels, Cation and Anion Exchange Membranes and Planar Geometry In this demonstration, an eluent generator with an anode-source channel, a product channel and a cathode-source channel was used. The anode-source and product channels were separated by a cation exchange membrane, and the product and cathode-source channels were separated by an anion exchange membrane. The device had planar geometry of the type generally illustrated in FIG. 5.

The eluent generator was constructed as follows. Cation exchange screen with integral gaskets and single-screen channel/electrode sub-assemblies were made as described in Example 1. Sub-assemblies were stacked inside the housing: single-screen channel/electrode sub-assembly on RAI 1010 cation exchange membrane on gasketed screen on RAI 1035 anion exchange membrane on single-screen channel/electrode sub-assembly.

The components functioned as follows. The top channel/electrode sub-assembly comprised the anode-source channel and contained the anode. The RAI 1010 cation exchange membrane separated the anode-source and product channels. The gasketed screen comprised the product channel. The RAI 1035 anion exchange membrane separated the product and cathode-source channels. The bottom channel/electrode sub-assembly comprised the cathode-source channel and contained the cathode.

The following external connections were made. The anode-source channel was fed with 250 mM sodium hydroxide at about 5 ml/min, and its effluent was directed to waste. The product channel was fed with deionized water at about 1 ml/min, and its effluent (the "product") was directed to chromatography instrumentation. The cathode-source channel was fed with deionized water at about 5 ml/min, and its effluent was directed to waste. The anode and cathode were connected to the positive and negative terminals, respectively, of a constant current power supply.

The following processes occurred in the eluent generator. In the anode-source channel, sodium hydroxide was oxidized according to the reaction:

$$4Na^+ + 4OH^- \rightarrow 4Na^+ + 2H_2O + O_2(g) + 4e^-.$$

Sodium ions in the anode-source channel passed across the cation membrane into the product channel to carry the current. In the cathode-source channel water was reduced according to the reaction:

$$4H_2O + 4e^- \rightarrow 4OH^- + 2H_2(g).$$

Hydroxide ions created in the cathode-source channel passed across the anion membrane into the product channel to carry the current. Thus sodium hydroxide was formed in the product channel. Purity of the sodium hydroxide product depended on the quality of the feed water and the ability of the membrane to exclude contaminants found in the sodium hydroxide feed.

Results were as follows. When the current was 50.0 mA and the voltage was 8.20 VDC, the device generated 31 mM sodium hydroxide at about 1 ml/min. When conditions were 100.1 mA and 10.7 VDC, it generated 48 mM sodium hydroxide at about 1 ml/min. When conditions were 149.5 mA and 12.5 VDC, it generated 74 mM sodium hydroxide at 1 ml/min.

EXAMPLE 4

Eluent Generator with Three Channels, Cation and Cation/Restrictor Exchange Membranes and Planar Geometry In this demonstration, an eluent generator with an anode-source channel, a product channel and a cathode-source channel was used. The anode-source and product channels were separated by a cation exchange membrane, and the product and cathode-source channels were separated by cation exchange/restrictor membrane. The device had planar geometry of the type generally illustrated in FIG. 5.

The eluent generator was constructed as follows. Platinum and stainless steel mesh screens with integral gaskets were prepared as described by EPA Pub. No. 180,321, published May 7, 1989. A restrictor was made by perforating an approximately 0.25 mm thick teflon sheet with about 0.5 to 0.7 mm diameter holes. Sub-assemblies were stacked inside the housing: gasketed platinum screen on Nafion 117 cation exchange membrane on gasketed cation exchange screen on Nafion 117 cation exchange membrane on restrictor on gasketed stainless steel screen.

The components functioned as follows. The gasketed platinum screen comprised the anode-source channel and the anode. The Nafion 117 membrane separated the anode-source and product channels. The gasketed cation exchange screen comprised the product channel. The Nafion 117 membrane and restrictor separated the product and cathode-source channels. The gasketed stainless steel screen comprised the cathode-source channel and the cathode.

The following external connections were made. The anode-source channel was fed with 175 mM sodium hydroxide at about 1.5 ml/min, and its effluent was directed to waste. The product channel was fed with deionized water at about 1 ml/min, and its effluent, the "product", was directed to chromatography instrumentation. The cathode-source channel was fed with deionized water at about 1.5 ml/min, and its effluent was directed to waste. The anode and cathode were connected to the positive and negative terminals, respectively, of a constant current power supply.

The following processes occurred in the eluent generator. In the anode-source channel, sodium hydroxide was oxidized according to the reaction:

$$4Na^+ + 4OH^- \rightarrow 4Na^+ + 2H_2O + O_2(g) + 4e^-.$$

Sodium ions in the anode-source channel passed across the cation membrane into the product channel to carry the current. In the cathode-source channel water was reduced according to the reaction:

$$4H_2O + 4e^- \rightarrow 4OH^- + 2H_2(g).$$

Hydroxide ions created in the cathode-source channel builds up to such concentrations as to overcome the Donnan barrier and pass across the restrictor and cation membrane into the product channel to carry the current. Thus sodium hydroxide was formed in the product channel. Purity of the sodium hydroxide product depends on the quality of the feed water and the ability of the membrane to exclude contaminants found in the sodium hydroxide feed.

Results were as follows. When the current was 100 mA and the voltage was 9 VDC, the device generated 24.6 mM sodium hydroxide at about 1 ml/min. When conditions were 50 mA and 7.8 VDC, it generated 12 mM sodium hydroxide at about 1 ml/min. When conditions were 25 mA and 7.0 VDC, it generated 6.3 mM sodium hydroxide at 1 ml/min.

EXAMPLE 5

Eluent Generator with Two Channels, One Cation Exchange Membrane and Tubular Geometry In this demonstration, an eluent generator with an anode-source channel and a product channel was used. The channels were separated by a cation exchange membrane. The device had tubular geometry of the type generally illustrated in FIG. 8.

The eluent generator was constructed as follows. A 0.38 mm diameter platinum wire was inserted into a 30 cm length of Nafion 811X cation exchange membrane tubing, forming a sub-assembly. The sub-assembly was inserted into a 28 cm length of 12 gauge, thin-wall, stainless steel tubing. Hydraulic connections were made to independently access the channels between the tubing as described by D. L. Strong and P. K. Dasgupta in Analytical Chemistry, vol. 61, pg. 939–945 (1989).

The components functioned as follows. The platinum wire was the anode. The lumen inside of the Nafion 811X tubing formed the anode-source channel. The Nafion 811X cation exchange membrane separated the anode-source and product channels. The annular space between the Nafion 811X tubing and the stainless steel tubing formed the product channel. The stainless steel tubing was the cathode.

The following external connections were made. The anode-source channel was fed with 250 mM sodium hydroxide at 1.5 ml/min, and its effluent was directed to waste. The product channel was fed with deionized water at 1 ml/min, and its effluent, the "product", was directed to a gas removal device and then to chromatography instrumentation. The anode and cathode were connected to the positive and negative terminals, respectively, of a constant current power supply.

The following processes occurred in the eluent generator. In the anode-source channel, sodium hydroxide was oxidized according to the reaction:

$$4Na+ + 4OH- \rightarrow 4Na+ + 2H2O + O2(g) + 4e-.$$

Sodium ions in the anode-source channel passed across the cation membrane into the product channel to carry the current. In the product channel water was reduced according to the reaction:

$$4H2O + 4e- \rightarrow 4OH- + 2H2(g).$$

Hydroxide ions thus created, along with sodium ions from the anode-source channel, formed sodium hydroxide product in the product channel. Purity of the sodium hydroxide product depended on the quality of the feed water and the ability of the membrane to exclude contaminants found in the sodium hydroxide feed.

Results were as follows. When the current was 200 mA and the voltage was 2.5 VDC, the device generated 112 mM sodium hydroxide at about 1 ml/min. When conditions were 300 mA and 2.7 VDC, it generated 168 mM sodium hydroxide at the same flow rate.

EXAMPLE 6

Eluent Generator with Three Channels, Cation and Anion Exchange Membranes and Tubular Geometry In this demonstration, an eluent generator with an anode-source channel, a product channel and a cathode-source channel was used. The anode-source and product channels were separated by a cation exchange membrane, and the product and cathode-source channels were separated by an anion exchange membrane. The device had tubular geometry of the type generally illustrated in FIG. 9.

The eluent generator was constructed as follows. A 0.38 mm diameter platinum wire was inserted into a 30 cm length of Nafion 811X cation exchange membrane tubing, forming the first sub-assembly. The first sub-assembly inserted into a 30 cm length of Toyo Soda 815X anion exchange membrane tubing, forming the second sub-assembly. The second sub-assembly was inserted into a 28 cm length of 12 gauge, thin-wall, stainless steel tubing. Hydraulic connections were made to independently access the channels between the tubing as described by D. L. Strong and P. K. Dasgupta in Analytical Chemistry, vol. 61, pg. 939-945 (1989).

The components functioned as follows. The platinum wire was the anode. The lumen inside of the Nafion 811X tubing formed the anode-source channel. The Nafion 811X cation exchange membrane separated the anode source and product channels. The annular space between the Nafion 811X tubing and the Toyo Soda 815X tubing formed the product channel. The Toyo Soda 815X anion exchange membrane separated the product and cathode-source channels. The annular space between the Toyo Soda 815X tubing and the stainless steel tubing formed the cathode-source channel. The stainless steel tubing was the cathode.

The following external connections were made. The anode-source channel was fed with 100 mM sodium hydroxide at 1.2 ml/min, and its effluent was directed to waste. The product channel was fed with deionized water at 0.5 ml/min, and its effluent, the "product", was directed to chromatography instrumentation. The cathode-source channel was supplied with deionized water at 1 ml/min, and its effluent was directed to waste. The anode and cathode were connected to the positive and negative terminals, respectively, of a constant current power supply.

The following processes occurred in the eluent generator. In the anode-source channel, sodium hydroxide was oxidized according to the reaction:

$$4Na+ + 4OH- \rightarrow 4Na+ + 2H2O + O2(g) + 4e-.$$

Sodium ions in the anode-source channel passed across the cation membrane into the product channel to carry the current. In the cathode-source channel water was reduced according to the reaction:

$$4H2O + 4e- \rightarrow 4OH- - 2H2(g).$$

Hydroxide ion created in the cathode-source channel passed across the anion membrane into the product channel to carry the current. Thus sodium hydroxide was formed in the product channel. Purity of the sodium hydroxide product depends on the quality of the feed water and the ability of the membrane to exclude contaminants found in the sodium hydroxide feed.

Results were as follows. When the current was 150 mA and the voltage was 3.6 VDC, the device generated 127 mM sodium hydroxide at about 0.5 ml/min. When conditions were 100 mA and 3.5 VDC, it generated 105 mM sodium hydroxide at the same flow rate.

What is claimed is:

1. Apparatus suitable for generating a high purity, aqueous product stream including one or more selected ionic species and using it as a chromatography eluent, comprising eluent generating means defining a source channel and a product channel, and comprising a permselective ion exchange membrane partitioning said source channel and product channel, said ion exchange membrane including exchangeable ions of the same charge as said selected ionic species and allowing transmembrane passage to ions of the same charge as said exchangeable ions and being resistant to transmembrane passage of ions of the opposite charge, means for applying an electrical potential between said source channel and product channel, chromatographic separating means, conduit means for directing aqueous product stream from said product channel to said chromatographic separation means, and means for supplying a liquid sample to said chromatographic separating means.

2. The apparatus of claim 1 further comprising programmable potential control means for automatically varying said electrical current applied in a timed sequence and correspondingly varying the concentration of said selected ionic species in said product stream.

3. The apparatus of claim 1 in which said one membrane comprises an essentially flat sheet.

4. The apparatus of claim 1 in which said one membrane comprises a tube and one of source and product channels comprises the lumen of said tube and the other one of said source and product channels comprises the annular space around said tube.

5. The apparatus of claim 1 further comprising gas removal means for selectively removing gas but not substantially removing liquid from said product liquid stream upstream of said chromatographic separating means.

6. The apparatus of claim 5 in which said gas removal means defines a product purification channel and a gas carrier channel separated by a gas diffusion membrane which permits transmembrane passage of the gas from said product stream.

7. The apparatus of claim 5 in which said gas removal means comprises a porous hydrophobic gas diffusion tube which permits the passage of gas but not substantially removing liquid from the product stream.

8. The apparatus of claim 1 further comprising bridging means disposed in said source channel comprising ion exchange means extending substantially across the source channel, said ion exchange means defining continuous convoluted liquid flow-through passages in said source channel along the length thereof the external surfaces of said ion exchange means including ion exchange sites with exchangeable ions of the same charge as the exchangeable ions of said one membrane sheet.

9. The apparatus of claim 8 in which said ion exchange means comprises a screen.

10. The apparatus of claim 8 in which said ion exchange means comprises ion exchange resin particles.

11. The apparatus of claim 1 in which said eluent generating means further defines a second source channel and further comprises a second membrane partitioning said product channel and said second source channel.

12. The apparatus of claim 11 where said second comprises a permselective ion exchange membrane including exchangeable ions of the opposite charge to those of said first membrane, said second membrane being resistant to transmembrane passage of selected ionic species and allowing transmembrane passage of ions of the opposite charge.

13. The apparatus of claim 11 where said second membrane comprises microporous membrane that offers greater resistance to the transport of the said selected ionic species than said first membrane such that a significant portion of the selected ionic species transported through the said first membrane into the said product channel remains in the said product channel.

14. The apparatus of claim 11 where said second membrane comprises a dialysis membrane.

15. The apparatus of claim 11 where said second membrane comprises an ion exchange membrane of the same charge type as the said first membrane and backed by an inert sheet defining a multiplicity of apertures.

16. A method of generating a high purity, aqueous product stream including one or more selected ionic species and using it as a chromatography eluent comprising the steps of (a) flowing an impure aqueous source solution containing said selected ionic species in hydroxide or acid form through a source channel separated by at least one permselective, ion exchange membrane from a product channel, said one membrane including exchangeable ions of the same charge as said selected one ionic species and allowing transmembrane passage to ions of the same charge as said exchangeable ions and being resistant to transmembrane passage of ions of the opposite charge, (b) flowing an aqueous stream through said product channel forming a product stream with said selected ionic species which passes across said one membrane, (c) applying an electrical potential between said source channel and product channel, electrode in said source channel being of the same charge as said selected ionic species and electrode in said product channel being of opposite charge, (d) directing said product stream, as an eluent, and liquid sample to liquid chromatographic separating medium, and (e) chromatographically separating components of said liquid sample on passage through said chromatographic separating medium.

17. The method of claim 16 in which said ionic species are cations and said product stream includes said cations in hydroxide form.

18. The method of claim 16 in which said ionic species are cations, and said aqueous stream flowing through said product channel includes anions, so that the product stream exiting said product channel comprises a salt of said cations and anions.

19. The method of claim 16 in which said ionic species are anions and said product stream includes said anions in acid form.

20. The method of claim 16 in which said ionic species are anions, and said aqueous stream flowing through said product channel includes cations, so that the product stream exiting said product channel comprises a salt of said anions and cations.

21. The method of claim 16 in which the application of said electrical potential is varied to vary the concentration of said ionic species in said product stream.

22. The method of claim 16 in which said selected ionic species comprises cations and hydroxide ion is generated electrolytically in said product channel.

23. The method of claim 16 in which said selected ionic species comprises anions and hydronium ion is generated electrolytically in said product channel.

24. The method of claim 16 in which said cations are selected from the group consisting of sodium, lithium, potassium, rubidium, cesium, ammonium, and tetralkyl ammonium.

25. The method of claim 24 in which gas is generated in said product stream in said product channel, said method further comprising the step of (f) removing said gas prior to step (d).

26. The method of claim 25 in which step (f) is accomplished by the step of (f) flowing said product stream containing electrolytically generated gas from said product channel to a product purification channel separated from a gas carrier channel by a gas diffusion membrane which permits transmembrane passage of the gas but prevents substantial passage of liquid from said product stream, and flowing a carrier stream through said gas carrier channel to entrain gas permeating across said gas diffusion membrane and remove it.

27. The method of claim 25 in which step (f) is accomplished by passing said product stream containing said gas through a porous hydrophobic gas diffusion tube permitting the transmembrane passage of said gas but not permitting substantial passage of the liquid portion of the product stream.

28. A method of generating a high purity, aqueous product stream including one or more selected ionic species and using it as a chromatographic eluent comprising the steps of
   (a) flowing an impure aqueous source solution containing said selected ionic species in hydroxide or acid form through a source channel separated by at least one permselective, ion exchange membrane from a product channel, said one membrane including exchangeable ions of the same charge as said selected ionic species and allowing transmembrane passage of ions of the same charge as said exchangeable ions and being resistant to transmembrane passage of ions of the opposite charge,
   (b) flowing an aqueous stream through said product channel forming a product stream with said selected ionic species which passes across said one membrane,
   (c) applying an electrical potential between said source channel and product channel, said source channel being of the same charge as said selected ionic species and said product channel being of opposite charge, and
   (d) systematically varying said electrical potential to vary the concentration of said selected ionic species in said product stream.
   (e) directing said product stream, as an eluent, and liquid sample to liquid chromatographic separating medium, and
   (f) chromatographically separating components of said liquid sample on passage through said chromatographic separating medium.

29. The method of claim 28 in which said ionic species are cations and said product stream includes said cations in hydroxide form.

30. The method of claim 28 in which said cations are selected from the group consisting of sodium, lithium, potassium, rubidium, cesium, ammonium, and tetralkyl ammonium.

31. A method of generating a high purity, aqueous product stream including one or more selected ionic species and using it as a chromatographic eluent comprising the steps of
   (a) flowing an impure aqueous source solution containing said selected ion in hydroxide or acid form through a source channel separated by a first permselective ion exchange membrane from a product channel, said first membrane including exchangeable ions of the same charge as said selected ionic species and allowing transmembrane passage of ions of the same charge as said exchangeable ions and being resistant to transmembrane passage of ions of the opposite charge,
   (b) flowing a high purity aqueous stream through said product channel forming a product stream with said selected ionic species which passes across said one membrane,
   (c) flowing an aqueous stream through a second source channel separated by a second permselective ion exchange membrane from said product channel, said second membrane including exchangeable ions of the opposite charge to those of said first membrane, said second membrane being resistant to transmembrane passage of selected ionic species and allowing transmembrane passage of ions of the opposite charge,
   (d) applying an electrical potential between said first source channel and said second source channel across said product channel, an electrode in said first source channel being of the same charge as said selected ionic species and electrode in said second source channel being of opposite charge,
   (e) directing said product stream as an eluent and liquid sample to liquid chromatographic separating medium, and
   (f) chromatographically separating components of said liquid sample on passage through said chromatographic separating medium.

32. The method of claim 31 in which said ionic species are cations and said product stream includes said cations in hydroxide form.

* * * * *